United States Patent
Garel et al.

(12) 
(10) Patent No.: US 6,479,690 B1
(45) Date of Patent: Nov. 12, 2002

(54) PHOSGENATION UNDER PRESSURE OF ALCOHOL'S FOR PRODUCING CHLOROFORMATES

(75) Inventors: Laurent Garel, Lyons; François Metz, Irigny, both of (FR)

(73) Assignee: Societe Nationale des Poudres et Explosifs, Paris (FR)

( * ) Notice: Subject to any disclaimer, the term of this patent is extended or adjusted under 35 U.S.C. 154(b) by 0 days.

(21) Appl. No.: 09/486,892

(22) PCT Filed: Aug. 31, 1998

(86) PCT No.: PCT/FR98/01867

§ 371 (c)(1),
(2), (4) Date: Mar. 6, 2000

(87) PCT Pub. No.: WO99/11597

PCT Pub. Date: Mar. 11, 1999

(30) Foreign Application Priority Data

Sep. 4, 1997 (FR) .......................................... 97 11189

(51) Int. Cl.$^7$ ............................................... C07C 69/96

(52) U.S. Cl. ....................... 558/280; 558/281; 558/282; 558/283

(58) Field of Search .................................. 558/280, 281, 558/282, 283

(56) References Cited

FOREIGN PATENT DOCUMENTS

| DE | 12 13 419 B | 3/1966 |
|---|---|---|
| EP | 542 132 A | 5/1993 |
| FR | 2 484 406 A | 12/1981 |

*Primary Examiner*—Paul J. Killos
(74) *Attorney, Agent, or Firm*—Pillsbury Winthrop LLP

(57) ABSTRACT

The invention concerns a method for phosgenation of monohydroxy alcohol's and/or polyols characterised in that it consists of treating alcohol and or polyol, whether in the presence of solvent or not, with a molar excess of phosgene, preferably 2 to 30 times more phosgene than the hydroxyl groups, at temperatures ranging between 0 and 200° C. and at pressure levels ranging between 2 and 60 bar, preferably in the absence of any catalyst. The method is further characterised in that pressure is further used to facilitate the separation of hydrochloric acid from phosgene, in a column external to the reactor.

8 Claims, 1 Drawing Sheet

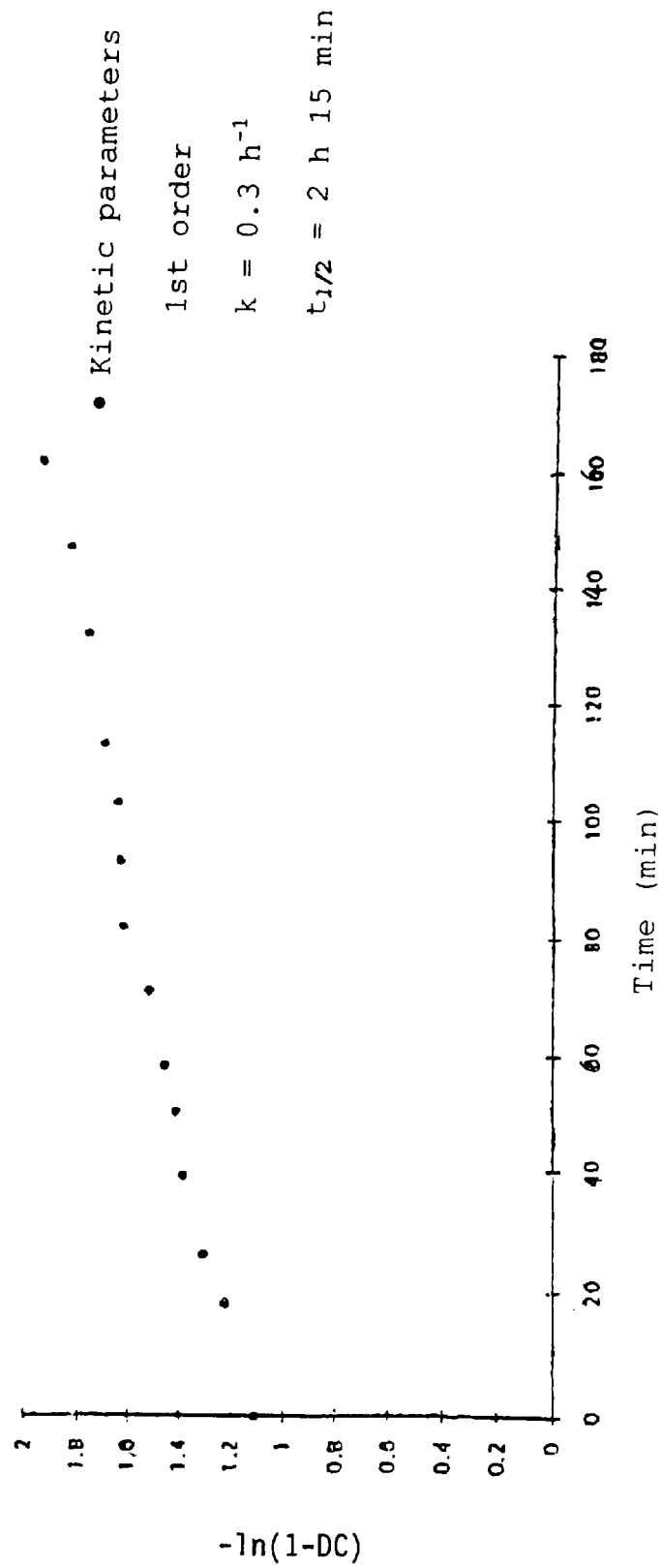
Figure 1: Phosgenation of isopropanol under pressure

PHOSGENATION UNDER PRESSURE OF ALCOHOL'S FOR PRODUCING CHLOROFORMATES

The present invention relates to a new process for obtaining chloroformates by phosgenating the corresponding alcohols under pressure with or without a catalyst, preferably in the absence of a catalyst.

Conventional processes consist in injecting phosgene into the alcohol, alone or in solution, under atmospheric pressure. In general, an excess of phosgene is used. The educts, consisting of a mixture of phosgene and hydrochloric acid, are inseparable under atmospheric pressure unless very low temperature condensers are used, which always results in a loss of phosgene.

The chemistry is governed by the following equation:

$$R(OH)_n + nCOCl_2 \rightarrow R(OCOCl)_n + nHCl \quad (k)$$

In order to activate the reaction, it is necessary to employ one or more catalysts; consequently, there is numerous literature concerning these derivatives. The use of a catalyst, however, presents a number of disadvantages. Foremost among these is their cost, followed by their influence on the choice of materials, since the catalysts often make the reaction system highly corrosive. Further, the catalyst promotes the formation of by-products and the development of discoloration. Finally, it necessitates purification of the chloroformate by distillation or crystallization.

The aim of the invention is to avoid the abovementioned disadvantages that are associated, in particular, with the use of catalysts.

The invention provides a process for phosgenating monohydroxy alcohols and/or polyols to obtain the corresponding chloroformates, characterized in that the alcohol and/or polyol are/is treated in the presence or absence of solvent with a molar excess of phosgene, preferably from approximately 2 to 30 times more phosgene per hydroxyl group, at a temperature of between 0 and 200° C. and at a pressure of between 2 and 60 bar (1 bar $=10^5$ Pa) with or without a catalyst, preferably in the absence of any catalyst. The process is generally carried out in a closed system (autogenous pressure) or in an open system (pressure regulated by partial degassing, for example). The process is generally operated continuously or semicontinuously. It is preferred to operate in an open system with partial degassing. Degassing must be carried out while ensuring that an excess of phosgene remains. This is done either by selective removal of the hydrochloric acid, while retaining the excess of phosgene and a little HCl, or by a degassing which includes the phosgene, with the latter being resupplied at the same time. The temperature is advantageously selected between 20 and 150° C., preferably between 25 and 80° C., while the pressure is selected preferably between 6 and 40 bar. The temperature and pressure conditions are determined by the nature of the alcohol and/or polyol and of the corresponding chloroformate, in particular by the critical point and/or decomposition point.

The advantages of the pressure phosgenation according to the invention are to be able a) to make it possible to do away with the low temperature condensers, b) to do away with solvent and/or catalyst, and c) to obtain chloroformates with little or no by-products such as carbonates and chlorides. This makes it possible to avoid final purification of the resulting chloroformate, to have a simple separation at the end of the reaction, and to reduce the cost of utilities, the advantages, in general terms, being those already discussed above and linked with the absence of catalyst.

The process according to the invention is advantageously employed for converting alcohols and/or polyols of formula $R(OH)_n$ to chloroformates $R(OCOCl)_n$, n being an integer from 1 to 6 and R being defined as follows:

- a saturated or unsaturated, linear or branched aliphatic radical having 1 to 22 carbon atoms which is optionally substituted a) by one or more identical or different halogen atoms, b) by one or more nitro groups, or c) by at least one alkyloxy, aryl (preferably phenyl), aryloxy or arylthio group, each of these groups being unsubstituted or substituted;
- a saturated or unsaturated, linear or branched polyoxyalkylene radical which is optionally substituted by the substituents indicated above and has a molecular mass of between 200 and 6000 (with the proviso that the alcohols are liquid or can be dissolved under the reaction conditions);
- a cycloaliphatic radical having 3 to 8 carbon atoms which bears or does not bear one or more substituents selected from a) halogen atoms, b) alkyl or haloalkyl radicals, c) nitro groups and d) aryl (preferably phenyl), aryloxy or arylthio radicals, it being possible for these radicals themselves to be unsubstituted or substituted;
- an aromatic carbocyclic radical which is unsubstituted or substituted by one or more substituents selected from the group consisting of halogen atoms, alkyl or haloalkyl radicals (preferably $CF_3$) having 1 to 12 carbon atoms (for example $C_2$-$C_6$ alkenyl, $C_3$-$C_8$ cycloalkyl, $C_4$-$C_{10}$ cycloalkylalkyl, $C_7$-$C_{10}$ aralkyl and $C_7$-$C_{10}$ aralkoxy), alkylthio or haloalkylthio radicals having 1 to 6 carbon atoms, alkylsulphinyl or haloalkylsulphinyl radicals having 1 to 6 carbon atoms, alkylsulphonyl or haloalkylsulphonyl radicals having 1 to 6 carbon atoms, alkyloxy or haloalkyloxy radicals having 1 to 6 carbon atoms, aryl, arylthio or aryloxy radicals, and the nitro group;
- a 5- or 6-membered aromatic or nonaromatic heterocyclic radical having one or more identical or different heteroatoms selected from oxygen, sulphur and nitrogen atoms and being unsubstituted or substituted by one or more substituents selected from halogen atoms, nitro groups, alkyl, haloalkyl, alkyloxy, haloalkyloxy, aryl, arylthio and aryloxy radicals and/or being optionally condensed with an aromatic carbocycle which itself is unsubstituted or substituted.

In general, when an aryl group (or one of its derivatives such as aryloxy or arylthio) or an aromatic carbocycle is mentioned, it should be considered, even if not stated at the time when such a radical appears, in order to lighten the present specification, that the said group or carbocycle can bear substituents selected from the group consisting of halogen atoms and alkyl, haloalkyl, alkyloxy, haloalkyloxy, alkylthio, haloalkylthio, alkylsulphinyl, haloalkylsulphinyl, alkylsulphonyl, haloalkylsulphonyl, aryl, aryloxy, arylthio and nitro radicals.

The process according to the invention is also suitable for converting mixtures of monohydroxy alcohols and/or mixtures of monohydroxy alcohols and polyols to corresponding chloroformates.

This process according to the invention is likewise characterized in that the pressure is further used to facilitate the separation of the hydrochloric acid and the phosgene in a column external to the reactor, without employing low temperature condensers which are, as has already been seen, a source of $COCl_2$ losses. The separation hence becomes more simple, and thus more economic, than with the known processes, and leads to readily recyclable phosgene and to pure hydrochloric acid.

The examples which follow are given purely by way of illustration of the invention, which they do not limit in any way whatsoever.

Process for preparing chloroformates by pressure phosgenation of monohydroxy alcohols These examples demonstrate the advantages linked to the process according to the invention, which was monitored by a two-dimensional field gradient NMR method. Kinetic monitoring was also carried out.

The NMR analyses under pressure were carried out on an AMX 300 spectrometer operating at 300 MHz for the proton and equipped with a 5 mm z-gradient QNP $^1H/^{13}C/^{19}F/^{31}P$ probe. The chemical shifts ($\delta$) of the proton and carbon resonance signals are expressed in ppm relative to deuterated DMSO (39.5 ppm in $^{13}C$ NMR and 2.24 ppm in $^1H$ NMR). For this example and for the following examples, the monocrystalline sapphire tube has internal and external diameters of 4 and 5 mm respectively.

The alcohol is introduced into this tube along with a capillary containing deuterated DMSO, in order to ensure field/frequency lock. The titanium head is fitted onto the tube, which is then immersed in a dry-ice/acetone bath (–78° C.) so as to condense the phosgene (which is introduced via a valve situated atop the head of the tube). The medium is allowed to return to ambient temperature (approximately 15 minutes) before the NMR measurements are conducted.

EXAMPLE 1

Phosgenation of benzyl alcohol

In accordance with the general procedure described above, 98.4 mg (0.89 mmol) of alcohol and 302.3 mg (3.05 mmol) of phosgene are introduced into the tube, corresponding to a phosgene/alcohol molar ratio of 3.4. The phosgene serves additionally as solvent.

Besides phosgene, the following three compounds were characterized: alcohol, chloroformate and benzyl chloride.

On the other hand, no benzyl carbonate was formed. It is therefore seen that, in addition to the fact that the chloroformate is produced under good conditions, the two other advantages of this process reside in the possibility of preventing or limiting the production of carbonate and chloride.

The NMR peaks of the $CH_2$ protons of the three abovementioned products are readily separated and identified. The intensity of these characteristic signals is monitored over time. The study is conducted at 300 K, and from the very first spectra it is noted that the degree of conversion of the benzyl alcohol is high: greater than 90% (cf. table below). The results show that the chloroformate forms rapidly and predominantly.

| Time (min) | Molar proportions, % | | |
|---|---|---|---|
| | Benzyl alcohol | Chloroformate | Benzyl chloride |
| 0* | 7 | 92 | 1 |
| 5 | 6 | 93 | 1 |
| 17 | 3 | 95 | 2 |
| 53 | 1 | 96 | 3 |
| 80 | <1 | 97 | 3 |

*this time t = 0 corresponds to the end of recording of the 1st proton spectrum

EXAMPLE 2

Phosgenation of isopropanol

In accordance with the general procedure described above, 66.2 mg (1.09 mmol) of alcohol and 186.0 mg (1.88 mmol) of phosgene are introduced into the tube, corresponding to a phosgene/alcohol molar ratio of 1.7. The phosgene serves additionally as solvent.

Besides phosgene, the following three compounds characterized: alcohol, chloroformate and isopropyl chloride.

The NMR sextuplets of the CH protons of the three abovementioned products are readily separated and identified. The intensity of these characteristic signals is monitored over time. The study is conducted at 300 K, and from the very first spectra it is noted that the degree of conversion of the isopropanol is high: greater than 70% (cf. table below). The results show that the chloroformate forms rapidly and predominantly.

| Time (min) | Molar proportions, % | | |
|---|---|---|---|
| | Isopropanol | Chloroformate | Isopropyl chloride |
| 0* | 33.0 | 67.0 | — |
| 18 | 29.4 | 70.6 | — |
| 39 | 24.8 | 73.9 | 1.3 |
| 50 | 24.0 | 74.5 | 1.5 |
| 82 | 19.3 | 78.4 | 2.3 |
| 113 | 17.7 | 79.1 | 3.2 |
| 162 | 13.7 | 82.3 | 4.0 |
| 232 | 11.3 | 82.1 | 6.6 |

* this time t = 0 corresponds to the end of recording of the 1st proton spectrum Plotting the negative natural logarithm of the quantity 1-DC (where DC = degree of conversion =(100 molar % of isopropanol)/100) as a function of time gives a straight line (cf. FIG. 1). The apparent order of the reaction of formation of chloroformate from isopropanol is therefore 1. The slope of this straight line is equal to the rate constant of the reaction: k =0.3 $h^{-1}$. The half-life time $t_{1/2}$, which represents the time required for the isopropanol concentration to reduce by half, is equal to 1n2/k ($t_{1/2}$=approximately 2 h 15 min).

Process for preparing chloroformates by pressure phosgenation of diols

The NMR analyses under pressure were carried out on an AMX 300 spectrometer operating at 300 MHz for the proton and equipped with a 5 mm z-gradient QNP $^1H/^{13}C/^{19}F/^{31}P$ probe. The chemical shifts ($\delta$) of the proton and carbon resonance signals are expressed in ppm relative to-deuterated DMSO (39.5 ppm in $^{13}C$ NMR and 2.24 ppm in $^1H$ NMR). For this example and for the following examples, the monocrystalline sapphire tube has internal and external diameters of 4 and 5 mm respectively.

The polyol is introduced into this tube along with a capillary containing deuterated DMSO, in order to ensure field/frequency lock. The titanium head is fitted onto the tube, which is then immersed in a dry-ice/acetone bath (–78° C.) so as to condense the phosgene (which is introduced via a valve situated atop the head of the tube). The medium is allowed to return to ambient temperature (approximately 15 minutes) before the NMR measurements are conducted.

EXAMPLE 3

Phosgenation of ethylene glycol under pressure

In accordance with the general procedure described above, 105.1 mg (1.69 mmol) of ethylene glycol and 1006 mg (10.2 mmol) of phosgene are introduced into the tube, corresponding to a phosgene/glycol molar ratio of 6. The phosgene serves additionally as solvent.

The reaction at 300 K is monitored by proton NMR and the phosgenation products are identified by one- and two-dimensional carbon and proton NMR.

After approximately 20 minutes of reaction at 300 K (between the end of preparation of the tube and the first proton NMR analysis), 62 molar % of dichloroformate (1), 14 molar % of carbonate (2) and 23 molar % of product (3) =ClCOO(CH$_2$)$_2$Cl are observed. No ethylene glycol is observed. The structure of the products formed is confirmed by gas chromatography/infrared/mass spectrometry analysis.

The results show that the dichloroformate is formed rapidly and predominantly.

| Time (min) | Molar proportions, % | | |
|---|---|---|---|
| | (1) | (2) | (3) |
| 20 | 62 | 14 | 23 |
| 38 | 66 | 18 | 16 |
| 100 | 70 | 20 | 9 |
| 163 | 71 | 23 | 5 |
| 355 | 70 | 27 | 2 |

EXAMPLE 4

Phosgenation of a polyethylene glycol (PEG) under pressure

In accordance with the general procedure described above, 113.8 mg (0.28 mmol) of polyethylene glycol and 576.6 mg (5.82 mmol) of phosgene are introduced into the tube, corresponding to a phosgene/PEG molar ratio of 20.8. The phosgene serves additionally as solvent.

The polyethylene glycol (PEG) chosen has a mass of approximately 400 M.

After approximately 20 minutes of reaction at 300 K (between the end of preparation of the tube and the first proton NMR analysis), 4 multiplets are observed:
- 1 peak at 3.59 ppm corresponding to the "central" OCH$_2$ protons of the PEG
- 1 multiplet at 3.71 ppm, with an intensity of 2
- 1 multiplet at 4.39 ppm, with an intensity of 2
- 1 broad multiplet at approximately 4.8, with an intensity of 1

This spectrum does not change at 300 K over 3 hours. Subsequently, we heated the system at 373 K for approximately 1 hour; we still obtained the same spectrum.

This allows us to consider that we have:
- either the product (4) where R' is probably OH, although R'=Cl cannot be excluded.

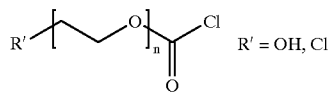

(4)     R' = OH, Cl

- or an equimolar mixture of PEG and "dichloroformate".

The first hypothesis appears the most likely. The structure of the products formed cannot be confirmed by gas chromatography/infrared/mass spectrometry analysis, since the mass of the compounds is too high.

Process for preparing chloroformates by pressure phosgenation of aromatic alcohols The NMR analyses under pressure were carried out on an AMX 300 spectrometer operating at 300 MHz for the proton and equipped with a 5 mm z-gradient QNP $^1$H/$^{13}$C/$^{19}$F/$^{31}$P probe. The chemical shifts (δ) of the proton and carbon resonance signals are expressed in ppm relative to deuterated DMSO (39.5 ppm in $^{13}$C NMR and 2.24 ppm in $^1$H NMR). For this example and for the following examples, the monocrystalline sapphire tube has internal and external diameters of 4 and 5 mm respectively.

The alcohol is introduced into this tube along with a capillary containing deuterated DMSO, in order to ensure field/frequency lock. The titanium head is fitted onto the tube, which is then immersed in a dry-ice/acetone bath (−78° C.) so as to condense the phosgene (which is introduced via a valve situated atop the head of the tube). The medium is allowed to return to ambient temperature (approximately 15 minutes) before the NMR measurements are conducted.

EXAMPLE 5

Phosgenation of phenol under pressure

In accordance with the general procedure described above, 43 mg (0.45 mmol) of phenol and 783 mg (7.9 mmol) of phosgene were introduced into the tube, corresponding to a phosgene/phenol molar ratio of 18. The phosgene serves additionally as solvent.

The sapphire tube was heated for approximately 10 h at 403 K (130° C.) and then for 7 h at 413 K (140° C.) in a silicone oil bath.

After heating at 413 K, in the proton and the carbon NMR, we observe the appearance of peaks of low intensity which are compatible with the presence of phenyl chloroformate (the chemical shifts of the proton and carbon 13 resonance peaks are indicated below for a product whose molar purity is estimated to be greater than 98%)

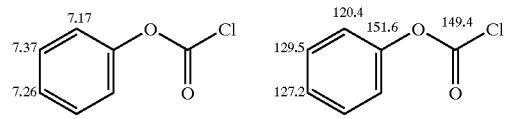

EXAMPLE 6

Phosgenation of 2-naphthol under pressure

In accordance with the general procedure described above, 31 mg (0.21 mmol) of 2-naphthol, 537 mg (5.4 mmol) of phosgene, corresponding to a phosgene/naphthol molar ratio of 26, and 688 mg (6.1 mmol) of chlorobenzene are introduced into the tube.

The 2-naphthol introduced is completely soluble in the chlorobenzene at 300 K. At 300 K, no reaction of the 2-naphthol is observed. At 393 K, after 5 h, the appearance of NMR signals of low intensity is observed, which we did not identify but which are compatible with the presence of 2-naphthyl chloroformate.

Process for preparing chloroformates by pressure phosgenation in a 2 litre autoclave

EXAMPLE 7

Preparation of n-octyl chloroformate

In a 2 litre autoclave, which is dried previously and is equipped with a condenser fed with glycolated water at −15° C. and equipped with a pressure regulation system, 890 g of monochlorobenzene are introduced and then 594 g (6 mol) of liquid phosgene are added, during which the reactor is cooled. This is followed by the rapid introduction of 130 g (1 mol) of n-octanol, and the air connection valve is closed. The reaction medium is heated to 50° C. The relative pressure reached is 3.2 bar. Argon is added to give a relative pressure of 11.5 bar, and then the reaction mixture is held at 50° C. for 1 hour. Pressure regulation at 11.2 bar (relative) takes place without further addition of argon. The reaction medium is subsequently cooled to approximately 20° C. and decompressed.

Analysis of the reaction medium by $^1$H NMR shows that n-octyl chloroformate has formed and there is no residual alcohol, no ether and no carbonate. Analysis by gas chromatography indicates a 1-chlorooctane content of 0.3 molar %, giving an estimated purity of the n-octyl chloroformate of 99.7%.

EXAMPLE 8

Preparation of the chloroformate of a heavy alcohol

In the present example, the alcohol phosgenated is polyoxybutylene alcohol 1616 (POBA) from the company Dow Chemical, having an average molar mass of 1400 and the following formula:

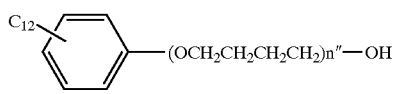

In the 2 litre autoclave, which is equipped and dried as in Example 7, the monochlorobenzene (500 g) is charged and 141 g of phosgene (1.42 mol) are introduced, during which the reaction medium is cooled with water. Subsequently, via a pump, 200 g of polyoxybutylene alcohol (0.143 mol) in solution in 400 g of monochlorobenzene are introduced and the air connection is closed. The reaction medium is heated to 60° C. The relative pressure reaches 10 bar. The relative pressure is then raised to 11.5 bar by adding argon under pressure. These conditions are maintained for 4 hours. The regulation of relative pressure takes place to 11.2 bar. The system is cooled to ambient temperature, at which point the relative pressure is 8.8 bar, and the reaction medium is decompressed. 1214 g are obtained, for a theoretical mass of 1232.1 g.

NMR monitoring is not possible. The yield of the synthesis is determined by assaying the proportion of phosgene and the proportion of hydrolysable chlorine on an aliquot of reaction medium.

After degassing and concentration, the proportion of hydrolysable chlorine is 3.58% and the proportion of phosgene is 4.46%, corresponding to 0.126 mol of chloroformate.

The yield in terms of chloroformate of the polyoxybutylene alcohol is 88%.

Infrared identification: presence of the CO band at 1781 cm$^{-1}$.

The colour of the resulting product is comparable to that of the starting alcohol.

EXAMPLE 9

Preparation of 2-perfluorohexylethyl chloroformate

In the 2 litre autoclave, treated and equipped as before, 600 ml of monochlorobenzene and 85 g of phosgene are introduced, during which the reactor is cooled.

The reactor is closed and cooled to 0° C., and 50 g of 2-perfluorohexylethanol are introduced under subatmospheric pressure. Nitrogen is added to give an absolute pressure of 12 bar and then the reaction medium is heated at 75° C. for 2 hours during which pressure regulation is maintained.

The reactor is subsequently decompressed and the reaction medium is distilled under reduced pressure in order to remove the monochlorobenzene. 30.5 g of concentrate are collected, containing a mixture of 80 g of 2-perfluorohexylethyl chloroformate and 20 g of di-2-perfluorohexylethyl carbonate.

What is claimed is:

1. Process for phosgenating monohydroxy alcohols and/or polyols to obtain the corresponding chloroformates, which comprises reacting the alcohol and/or polyol in the presence or absence of solvent with a molar amount of phosgene of at least 3.4 per hydroxyl group, at a temperatures of between 0 and 200° C. and at a pressure of between 2 and 60 bar without a catalyst.

2. Process according to claim 1 wherein the reaction is carried out with up to 30 times more phosgene relative to each hydroxyl group.

3. Process according to claim 1 or 2, wherein the reaction is carried out in an open system with partial degassing.

4. Process according to claim 1 or 2 wherein the reaction temperature is between 20 and 150° C.

5. Process according to claim 1 wherein the pressure is between 6 and 40 bar.

6. Process according to claim 1 wherein an alcohol and/or polyol of formula $R(OH)_n$ is converted to a chloroformate $R(OCOCl)_n$, n being an integer from 1 to 6 and R being defined as follows:

- a saturated or unsaturated, linear or branched aliphatic radical having 1 to 22 carbon atoms which is optionally substituted a) by one or more identical or different halogen atoms, b) by one or more nitro groups, or c) by at least one alkyloxy, aryl, aryloxy or arylthio group, each of these groups being unsubstituted or substituted;

- a saturated or unsaturated, linear or branched polyoxyalkylene radical which is optionally substituted by the substituents indicated above and has a molecular mass of between 200 and 6000 (with the proviso that the alcohols are liquid or can be dissolved under the reaction conditions);

- a cycloaliphatic radical having 3 to 8 carbon atoms which bears or does not bear one or more substituents selected from a) halogen atoms, b) alkyl or haloalkyl radicals, c) nitro groups and d) aryl, aryloxy or arylthio radicals, it being possible for these radicals themselves to be unsubstituted or substituted;

- an aromatic carbocylic radical which is unsubstituted or substituted by one or ore substituents selected from the group consisting of halogen atoms, alkyl or haloalkyl radicals having 1 to 12 carbon atoms, $C_2$-$C_6$ alkenyl, $C_3$-$C_8$ cycloalkyl, $C_4$-$C_{10}$ cycloalkylalkyl, $C_7$-$C_{10}$ aralkyl and $C_7$-$C_{10}$ aralkoxy radicals, alkylthio or haloalkylthio radicals having 1 to 6 carbon atoms, alkylsulphinyl or haloalkylsulphinyl radicals having 1 to 6 carbon atoms, alkylsulphonyl or haloalkylsulphonyl radicals having 1 to 6 carbon atoms, alkyloxy or haloalkyloxy radicals having 1 to 6 carbon atoms, aryl, arylthio or aryloxy radicals, and the nitro group;

- a 5- or 6-membered aromatic or nonaromatic heterocyclic radical having one or more identical or different heretoatoms selected from oxygen, sulphur and nitrogen atoms and being unsubstituted or substituted by one or more substituents selected from halogen atoms, nitro groups, alkyl, haloalkyl, alkyloxy, haloalkyloxy, aryl, arylthio and aryloxy radicals and/or being optionally condensed with an aromatic carbocycle which itself is unsubstituted or substituted.

7. Process according to claim 1 or 2 wherein a mixture of monohydroxy alcohols is converted to chloroformates.

8. Process according to claim 1 or 2 wherein a mixture of monohydroxy alcohols and polyols is converted to chloroformates.

* * * * *